United States Patent [19]
Nakamichi et al.

[11] Patent Number: 5,811,547

[45] Date of Patent: Sep. 22, 1998

[54] METHOD FOR INDUCING CRYSTALLINE STATE TRANSITION IN MEDICINAL SUBSTANCE

[75] Inventors: Kouichi Nakamichi, Shiga; Shougo Izumi, Kyoto; Masaaki Oka, Osaka, all of Japan

[73] Assignee: Nippon Shinyaju Co., Ltd., Kyoto, Japan

[21] Appl. No.: 416,815

[22] PCT Filed: Oct. 13, 1993

[86] PCT No.: PCT/JP93/01469

§ 371 Date: Jun. 9, 1995

§ 102(e) Date: Jun. 9, 1995

[87] PCT Pub. No.: WO94/08561

PCT Pub. Date: Apr. 28, 1994

Related U.S. Application Data

[63] Continuation-in-part of Ser. No. 129,133, Nov. 15, 1993, Pat. No. 5,456,923.

[30] Foreign Application Priority Data

Oct. 14, 1992 [JP] Japan ..................... 4-303085

[51] Int. Cl.$^6$ ............ C07D 209/32; C07D 223/24
[52] U.S. Cl. ............ 540/589; 548/500; 564/45; 564/213
[58] Field of Search .............. 548/500; 564/45; 564/213; 540/589

[56] References Cited

U.S. PATENT DOCUMENTS

| | | | |
|---|---|---|---|
| 4,129,649 | 12/1978 | Inoue et al. | 424/182 |
| 5,160,680 | 11/1992 | Serpelloni et al. | 264/126 |
| 5,256,234 | 10/1993 | Mutaguchi et al. | 156/224.27 |
| 5,385,749 | 1/1995 | Serpelloni et al. | 426/658 |

FOREIGN PATENT DOCUMENTS

| | | |
|---|---|---|
| 0 177 428 | 10/1985 | European Pat. Off. . |
| 0 490 768 A1 | 12/1991 | European Pat. Off. . |
| 0 580 860 A1 | 4/1992 | European Pat. Off. . |
| 60-190723 | 9/1985 | Japan . |

OTHER PUBLICATIONS

Obandie et al, J. of Applied Polymer Science, vol. 37, pp. 1713–1726 (1989).

Journal of Pharamaceutical Sciences, vol. 62, No. 1, Jan. 1973 F.W. Goodhart, et al. "Design and Use of A Laboratory Extruder for Pharmaceutical Granulations", pp. 133–136.

*Primary Examiner*—Mukund J. Shah
*Assistant Examiner*—K. Wong
*Attorney, Agent, or Firm*—Graham & James LLP

[57] ABSTRACT

This invention has for its object to provide a method of inducing a transition in crystalline state of a crystallizable medicinal substance with great ease and improved efficiency and uniformity on a high production scale. According to the invention, an extruder is used for inducing a transition from one crystalline state ($\Delta$) to another crystalline state in a crystallizable medicinal substance.

12 Claims, 5 Drawing Sheets

METHOD FOR INDUCING CRYSTALLINE STATE TRANSITION IN MEDICINAL SUBSTANCE

This is a continuation in part application of U.S. Ser. No. 08/129,133, filed Nov. 15, 1993, now U.S. Pat. No. 5,456,923, issued Oct. 10, 1995, and is a 371 national filing of PCT/JP93/01469, filed Oct. 13, 1993.

TECHNICAL FIELD

This invention relates to a method of inducing a transition of crystalline state in a crystallizable medicinal substance.

As used in this specification, the term 'stable crystal' means any crystal that is in thermodynamically stable crystalline state and the term 'metastable crystal' means any crystal that is in thermodynamically unstable crystalline state. The term 'crystalline state' is used referring to any of stable crystal, metastable crystal and amorphous (noncrystalline) solid. The term 'heterogenous crystal' means a crystal not in a singular crystalline state.

The term 'extruder' means any screw extruder that is in broad use chiefly in food industry for the processing of food materials (cereals, proteins, animal meat, fish meat, etc.).

BACKGROUND ART

The conventional technology for inducing a transition of crystalline state in a medicinal substance includes recrystallization, heating, freeze-drying, pulverizing and so on.

However, none of these conventional methods are capable of inducing a transition of crystalline state expediently, efficiently, uniformly and on a mass scale and, therefore, are not well suited for commercial application. One of the reasons for their incapability is that because these technologies are invariably batch processes, large-scale equipment is required for mass processing but the larger the equipment, the greater is the temperature gradient created in the processing load, so that homogeneous crystals cannot be easily obtained. Taking the recrystallization process as an example, judicious selection of the recrystallization solvent, detailed analysis of recrystallizing temperature and other parameters, and accurate control of recrystallization conditions are essential. In the case of freeze-drying, the protracted processing time is also a detracting factor.

The present invention will be clearly seen from the following discussion and the drawings in which:

DISCLOSURE OF INVENTION

The object of this invention is to provide a method of inducing a transition of crystalline state in a crystallizable medicinal substance which overcomes the disadvantages of the above-mentioned prior art methods. Specifically, the invention has for its object to provide a method of inducing, expediently, efficiently, uniformly, continuously and on a high production scale, a transition of crystalline state, for example:

(1) from a crystallizable active substance in metastable crystalline state or in amorphous solid state to stable crystals, (2) a crystallizable active substance in stable crystalline state or in amorphous solid state to metastable crystals, (3) a crystallizable active substance in stable crystalline state or in metastable crystalline state to an amorphous solid, or (4) a crystallizable active substance in heterogenous crystalline state to homogeneous crystals.

The inventors of this invention found that the above-mentioned object can be accomplished by utilizing an extruder which enables a continuous processing of the load and have arrived at the present invention.

In the pharmaceutical field, few technologies utilizing an extruder are known.

Figure 1:
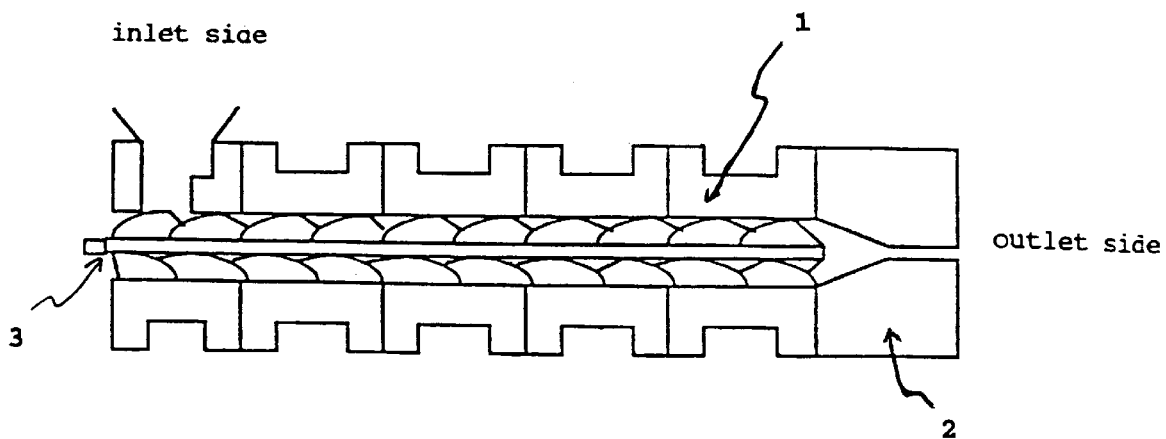
FIG. 1 is a schematic cross-section view of the main part of the extruder used to effect the method of the present invention.

At this junction, the mechanism of the main part (work processing part) of the extruder is briefly described. Generally the main part of an extruder comprises, as illustrated in FIG. 1, a cylindrical structure called 'barrel', a die which corresponds to a delivery port, and a screw. The barrel usually comprises a plurality of unit barrels and the screw extends through them. The screw is available in various types, namely trapezoidal screw, trapezoidal cut screw, trapezoidal reverse cut screw, ball screw, kneading paddle: etc., which can be used in a desired combination. The load fed to the extruder is forced by the screw to advance, shorn and blended by the screw within the barrel structure and extruded from the orifice or orifices of the die. Usually, the temperature of each unit barrel and that of the die can be independently controlled.

The extruder is available in two general types, namely a single-screw extruder comprising one screw and a multi-screw extruder comprising two or more screws. While this invention can be carried into practice using either type of extruder, the use of a multi-screw extruder, particularly a twin-screw extruder, is preferred. Compared with a single-screw version, a twin-screw extruder is more efficient in that the plural screws interferring with each other precludes follow-up movement of the active substance and, moreover, the intermeshing of the screws provides a high energy output physically, thus assisting in the induction of a transition of crystalline state.

In the practice of this invention, such an extruder as is in routine use by food industry can be utilized as it is.

The mode of use of the extruder in the practice of this invention is now described, referring to specific embodiments.

Figure 2:
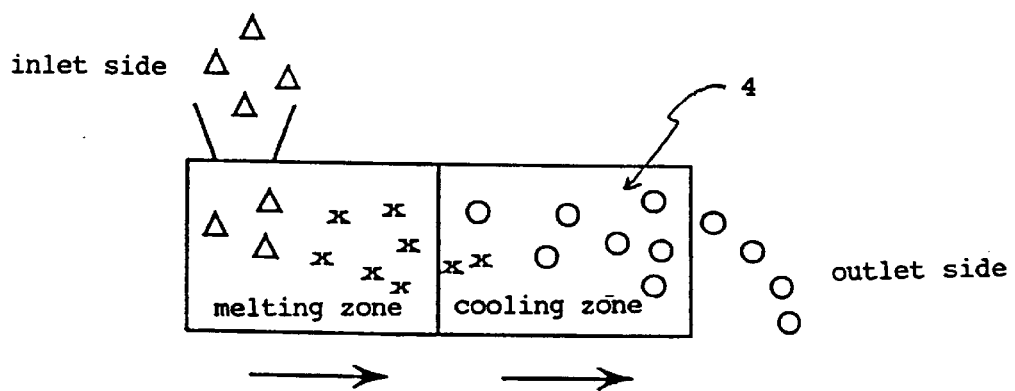
FIG. 2, is a schematic representation of change in crystalline state of the medical substance being processed in the extruder of FIG. 1.

For example, in this invention, the main part of the extruder can be utilized as divided into two zones, namely a melting zone and a cooling zone as illustrated in FIG. 2. The melting zone is the zone in which the medicinal substance is melted and the cooling zone is the zone in which the medicinal substance melted in said melting zone is solidified.

In the practice of this invention, the melting zone can be defined by one or more barrels. If and when the medicinal material can be successfully melted, even a single barrel can serve as the melting zone. However, the proper number of barrels defining the melting zone is dependent on the melting point of the medicinal substance, the crystalline state of said substance, the condition of the substance, the type and ratings of the extruder used, the rotational speed of the screw (which corresponds to the speed at which the medicinal load travels within the barrel), screw geometry (which is related to the pulverization of the medicinal substance) and so on. For the processing of a medicinal substance having a high melting point, in the case where the medicinal substance is crystalline or coarse, or for increasing the rotational speed of the screw, the number of barrels constituting the melting zone may have to be increased.

In the practice of this invention, the temperature of the barrel or barrels constituting the melting zone (hereafter referred to as 'melting zone temperature') can be set to the meltable temperature of the medicinal substance. However, the temperature setting is preferably equal to the melting point of the medicinal substance and more preferably the melting start temperature. If the melting zone temperature be too high, the medicinal substance might decompose. When the melting zone is defined by a plurality of barrels, the temperature of the respective barrels need not necessarily be uniform.

In this invention, the cooling zone can be constituted using the remaining barrels, viz. barrels other than the barrels defining the melting zone, and the die. Depending on cases, the environment (external zone) surrounding the extruder may be included in the cooling zone. Even when the external zone is included in the cooling zone, since the molten medicinal substance is delivered out continuously and little by little from the die orifices, there is substantially no concern about the loss of homogenity due to a temperature gradient.

The temperature settings of the barrel or barrels and die defining the cooling zone (hereinafter called 'cooling zone temperature') are now explained, taking the transition of various crystalline states as examples.

(1) The procedure for inducing a transition from metastable crystals to stable crystals, for instance, and the procedure for inducing a transition from hererogenous crystals to homogeneous crystals:

While the cooling zone temperature is dependent on the physical properties of the medicinal substance, the type and ratings of extruder used, etc., the cooling zone temperature can be set within the range of ambient temperature to a temperature below the melting-start temperature of stable crystals of the medicinal substance. It is practically useless to employ a temperature setting lower than ambient temperature, while the medicinal substance fails to crystallize at times when the setting exceeds the melting-start temperature of stable crystals of the medicinal substance. There are cases in which a transition to stable crystalline state can be obtained even when the setting is below ambient temperature and such cases also fall within the scope of this invention.

It is true that the higher the cooling zone temperature, the greater is the safety with which a medicinal substance can be crystallized. However, although it depends on physical properties of the medicinal substance, a higher cooling zone temperature setting may call for an increase in the overall length of the barrel defining the cooling zone or a reduction in the rotational speed of the screw. In either case, processing efficiency tends to be sacrificed. On the other hand, it is not recommendable, either, to use an unnecessarily low cooling zone temperature. If the cooling zone temperature setting is too low, an amorphous solid may result or the crystals may become heterogenous. Therefore, in order to insure an efficient and safe working of this invention, the cooling zone temperature is preferably selected in consideration of the physical properties of the medicinal substance, the type and ratings of extruder, melting zone temperature, and the rotational speed of the screw, among other factors.

The cooling zone temperature can be preset with the aid of a melting point measuring instrument equipped with a opticaly microscope (e.g. Mettler's, melting/boiling point meter Model FP-80 or FP-82HT equipped with a polarizing microscope), a differential scanning calorimeter (DSC) or the like. Thus, in the case of a melting point measuring instrument equipped with a opticaly microscope, one may use the method which comprises melting the medicinal substance on a slide glass, cooling it to find the temperature at which stable crystals are formed and using the particular temperature as the cooling zone temperature.

Where the cooling zone is defined by a plurality of unit barrels, the temperature settings of the respective barrels and of the die need not necessarily be identical. However, the temperature of the down stream barrel or the die is preferably set below the temperature of the upstream barrel. Reversing this relation will be in conflict with the direction of crystallization of the medicinal substance. moreover, in such cases, it is not a good practice to set the temperature of each barrel constituting the cooling zone at an unnecessarily low level relative to the temperature of the immediately preceding barrel (both of the melting zone and cooling zone). If said temperature setting is unnecessarily too low compared with the temperature of the immediately preceding barrel, an amorphous solid tends to form or heterogenous crystals may be produced. The system in which the cooling zone temperature is not uniform is instrumental where crystallization of the medicinal substance is desirably achieved by gradual cooling.

When the cooling zone temperature is set to ambient temperature, it is not essential to provide a cooling zone within the barrel structure. When the barrel structure has no cooling zone, the environment functions as a cooling zone and all the barrels and die constitute the melting zone.

(2) The procedure for inducing a transition from stable crystalline state or the like to metastable crystalline state and the procedure for inducing a transition from heterogenous crystalline state to metastable crystalline state:

The cooling zone temperature in these cases can be established beforehand with the aid of a melting point measuring instrument equipped with a opticaly microscope (e.g. Mettler's melting/boiling point meter Model FP-80 or FP-82HT equipped with a polarizing microscope), a differential scanning calorimeter (DSC) or the like. Thus, in the case of a melting point measuring instrument equipped with a opticaly microscope, the method can be used which comprises melting the medicinal substance on a slide glass, cooling it to find the temperature at which metastable crystals are formed and using the particular temperature as the cooling zone temperature.

Where the cooling zone is defined by a plurality of barrels, the temperature settings of the respective barrels and of the die need not necessarily be identical. However, the temperature of any downstream barrel or the die is preferably set below the temperature of the upstream barrel. Reversing this relation will be in conflict with the direction of crystallization of the medicinal substance. Moreover, in such cases, it is not a good practice to set the temperature of each barrel constituting the cooling zone at an unnecessarily low level relative to the temperature of the immediately preceding barrel (both of the melting zone and cooling zone). If said temperature setting is unnecessarily too low as compared with the temperature of the immediately preceding barrel, an amorphous solid tends to form or heterogenous crystals may be produced.

The system in which the cooling zone temperature is not uniform is instrumental where crystallization of the medicinal substance is desirably achieved by gradual cooling.

When the cooling zone temperature is set to ambient temperature, it is not essential to provide a cooling zone within the barrel structure. When the barrel structure has no cooling zone, the environment functions as a cooling zone and all the barrels and die constitute the melting zone.

(3) The procedure for inducing a transition from stable crystalline state or the like to amorphous solid state and the procedure for inducing a transition from heterogeneous crystalline state to homogeneously amorphous solid state:

By nature of an amorphous solid, the cooling zone temperature in these cases is preferably as low as possible. In this invention, although it depends on physical properties of the medicinal substance and the type and ratings of the extruder used, among other variables, the cooling zone temperature can be set to a temperature about 70% lower than the melting-start temperature of the medicinal substance (e.g. 30° C. where the melting-start temperature of the medicinal substance is 100° C. ) or even a still lower temperature. It is more preferable that the temperature setting be not higher than a level about 90% lower than the melting-start temperature of the medicinal substance. If the temperature setting is too high, the stable or metastable crystalline state will avail. Although the desired transition to amorphous solid state may be achieved at times even when the temperature setting is higher than said limit, such cases also fall within the scope of this invention.

The cooling zone temperature in these cases can be established beforehand with the aid of a melting point measuring instrument equipped with a opticaly microscope (e.g. Mettler's melting/boiling point meter Model FP-80 or FP-82HT equipped with a polarizing microscope), a differential scanning calorimeter (DSC) or the like. Thus, in the case of a melting point measuring instrument equipped with a opticaly microscope, the method can be used which comprises melting the medicinal substance on a slide glass, cooling it to find the temperature at which an amorphous solid is formed and using the temperature as the cooling zone temperature.

Where the cooling zone is defined by a plurality of barrels, the temperature settings of the respective barrels and of the die need not necessarily be identical. However, the temperature of any downstream barrel or the die is preferably set below the temperature of the upstream barrel. Reversing this relation will be in conflict with the direction of solidification of the medicinal substance.

When the cooling zone temperature is set to ambient temperature, it is not essential to provide a cooling zone within the barrel structure. When the barrel structure has no cooling zone, the environment functions as a cooling zone and all the barrels and die constitute the melting zone.

Feeding of the medicinal substance into the barrel structure can be performed by utilizing the feeder with which the extruder is generally provided but there is no limitation on the device that can be used only if the medicinal substance may be fed at a constant rate.

As examples of such feeding device, a screw feeder, a table feeder, a belt-conveyer type quantitative feeder, and an electromagnetic feeder can be mentioned.

Although the medicinal substance can be directly fed into the melting zone, it is a good practice to provide a feeding zone using an appropriate number of unit barrels and supply the medicinal substance to said zone in the first place. This is because the barrel adjacent to the inlet is exposed to the environment and, hence, not well amenable to temperature control. Only one barrel generally suffices for constituting said feeding zone and, by nature, its temperature may be equal to ambient temperature.

The rotational speed of the screw can be set within the allowable range of the extruder used. Generally speaking, assuming that the kind and shape of medicinal substance are unchanged, the rotational speed of the screw can be increased in the case of an extruder with a greater overall barrel length as compared with an extruder with a shorter overall barrel length.

The screw geometry and combination of unit screws can be selected without any particular restriction. The principal role of the screw in this invention is to transport, crush and knead the medicinal substance. Therefore, when the particle size of the feed medicinal substance is previously set to be such that it can be smoothly transported by the screw, it is substantially unnecessary to pay attention to the screw geometry.

The orifice configuration of the extrusion die is not particularly restricted and may for example be circular, elliptical, rectangular or hexagonal. When the orifice is circular in section, its diameter can be selected appropriately. For example, the range of 0.5–5 mm $\phi$ can be mentioned.

Whether the desired transition has been achieved or not can be verified by means of a opticaly microscope, a powder X-ray diffractometer, a differential scanning calorimeter (DSC) or the like.

As regards the crystallizable medicinal substance that can be used in this invention, there is no particular restriction only if it does not decompose on exposure to the melting-start temperature. This invention can be applied not only to medicinal substances but also to other crystallizable substances used in the fields of farm chemicals and food. The following specific crystallizable substances can be mentioned by way of example.

1. General anesthetics:
   Ketamine hydrochloride, thiamylal sodium, thiopental sodium, droperidol.
2. Hipnotic/sedatives/antianxiety drugs:
   Amobarbital, alprazolam, estazolam, flurazepam hydrochloride, rilmazafone hydrochloride, oxazepam, oxazolam, cloxazolam, clotiazepam, clorazepate dipotassium, chlordiazepoxide, chlormezanone, diazepam, secobarbital sodium, zopiclone, triazolam, triclofos sodium, nitrazepam, nimetazepam, barbital, haloxazolam, phenobarbital, prazepam, fludiazepam, flutazolam, flutoprazepam, flunitrazepam, flurazepam, brotizolam, bromazepam, bromovalerylurea, hexobarbital, perlapine, pnetobarbiturate, midazolam, mexazolam, medazepam, ethyl loflazepate, lorazepam, lormetazepam.
3. Antiepileptics:
   Acetylpheneturide, ethosuximide, ethotoin, carbamazepine, clonazepam, sultiame, zonisamide, trimethadione, sodium valproate, phenytoin sodium, primidone, metharbital.
4. Antipyretic/analgesic/antiinflammatory agents:
   Aspirin, aspirin DL-lysine, aspirin aluminum, acetaminophen, acemetacin, alclofenac, aiminoprofen, amfenac sodium, isopropylantipyr ine, ibuprofen, indomethacin, indomethacin farnesil, ethenzamide, epirizole, emorfazone, tiaramide hydrochloride, tinoridine hydrochloride, tramadol hydrochloride, buprenorphine hydrochloride, benzydamine hydrochloride, oxaprozin, clofezone, ketophenylbutazone, ketoprofen, sasapyrine, salicylamide, choline salicylate, sodium salicylate, Saridon, diclofenac sodium, diflunisal, eptazocine hydrobromide, butorphanol tartrate, sulindac, sulpyrine, tiaprofenic acid, tenoxicam, tolfenamic acid, tolmetin sodium, nabumetone, naproxen, Neo vitacain, Neurotropin, bitoxin, piroxicam, phenacetin, phenylacetylglycine, phenylbutazone, fenoprofen calcium, fenbufen, bucolome, pranoprofen, flufenamic acid, flufenamic acid aluminium, flurbiprofen, flurbiprofenaxetil, floctafenine, pentazocine, proglumetacin maleate, migrenin, dimetotiazine mesilate, metiazinic acid, mefenamic acid, loxoprofen sodium, lobenzarit disodium.

5. Analeptic/antihypnotic agents:
Methamphetamine hydrochloride, bemegride.

6. Antiparkinsonian drugs:
Amantadine hydrochloride, trihexyphenidyl hydrochloride, piroheptine hydrochloride, mazaticol hydrochloride, methixene hydrochloride, droxidopa, biperiden, bromocriptine mesilate, levodopa.

7. Psychotropic/neurotropic drugs:
Amoxapine, etizolam, amitriptyline hydrochloride, imipramine hydrochloride, clocapramine dihydrochloride, clomipramine hydrochloride, safrazine hydrochloride, sultopride hydrochloride, thioridazine hydrochloride, desipramine hydrochloride, dosulepin hydrochloride, trazodone hydrochloride, triflupromazine hydrochloride, nortriptyline hydrochloride, hydroxyzine hydrochloride, pipamperone hydrochloride, pipradorol hydrochloride, maprotiline hydrochloride, mianserin hydrochloride, methylphenidate hydrochloride, mosapramine hydrochloride, moperone hydrochloride, lofepramine hydrochloride, oxypertine, carpipramine, clotiapine, chlorprothixene, chlorpromazine, thioproperazine dimethansulfonate, spiperone, sulpiride, zotepine, tiotixene, timiperone, haloperidol decanoate, nemonapride, hydroxyzine pamoate, haloperidol, pimozide, fluphenazine, prochlorperazine, propericyazine, bromazepam, bromperidol, pemoline, perphenazine, cetiprin maleate, trifluoperazine maleate, trimipramine maleate, reserpine, levomepromazine.

8. CNS drugs:
Idebenone, amantadine hydrochloride, indeloxazine hydrochloride, cyproheptadine hydrochloride, tiapride hydrochloride, bifemelane hydrochloride, meclofenoxate hydrochloride, lefetamine hydrochloride, γ-amino-β-hydroxybutyric acid, citicoline, protirelin tartrate, baclofen, propentofylline, calcium hopantenate, mazindol.

9. Local anesthetics:
Ethyl aminobenzoate, oxybuprocaine hydrochloride, dibucaine hydrochloride, tetracaine hydrochloride, p-butylaminobenzoyldiethyl aminoethanol hydrochloride, bupivacaine hydrochloride, procaine hydrochloride, propitocaine hydrochloride, mepivacaine hydrochloride, oxethazaine, ethyl p-piperidinoacetyl aminobenzoate, lidocaine hydrochloride.

10. Skeletal muscle relaxants:
Alcuronium chloride, suxamethonium chloride, tubocurarine chloride, chlorphenesin carbamate, chlorzoxazone, chlormezanone, pancuronium bromide, vecuronium bromide, dantrolene sodium, phenprobamate, pridinol mesylate, methocarbamol.

11. Autonomic drugs:
Acetylcholine chloride, ambenonium chloride, carpronium chloride, trospium chloride, bethanechol chloride, oxyphencyclimine hydrochloride, dicycloverin hydrochloride, tolazoline hydrochloride, distigmine bromide, valethamate bromide, pyridostigmine bromide, prifinium bromide, propantheline bromide, mepenzolate bromide, tofisopam, aclatonium napadisilate, neostigmine, oxapium iodide, diphenylpiperidinomethyldioxolane iodide.

12. Antispasodics:
Afloqualone, etomidoline, isoxsuprine hydrochloride, eperisone hydrochloride, tizanidine hydrochloride, tolperisone hydrochloride, papaverine hydrochloride, piperidolate hydrochloride, bromoethyl pipethanate, scopolamine hydrobromide, timepidium bromide, valethamate bromide, butylscopolamine bromide, atropine methobromide, anisotropine methobromide, benactyzium methobromide, baclofen, flopropione, metyrapone, N-methyl-scopolamine methyl sulfate, atropine sulfate.

13. Antivertigo drugs:
Isoprenaline hydrochloride, difenidol hydrochloride, meclizine hydrochloride, dimenhydrinate, thiethylperazine, promethazine theoclate and, betahistine mesylate.

14. Sense organ drugs:
Oxymetazoline hydrochloride, tetrizoline.

15. Cardiotonics:
2-Aminoethanesulfonic acid, aminophylline, caffeine-sodium benzoate, etilefrine hydrochloride, ephedrine hydrochloride, dopamine hydrochloride, dobutamine hydrochloride, bucumolol hydrochloride, choline theophylline, diisobutylaminobenzoyloxypropyl theophylline, digitoxin, digoxin, diprophylline, metaraminol bitartrate, deslanoside, denopamine, trans-π-oxocamphor, bucladesine sodium, proxyphylline, proscillaridin, besnalinone, metildigoxin, ubidecarenone, lanatoside C.

16. Antiarrhythmic drugs:
Ajmaline, atenolol, acebutolol hydrochloride, aprindine hydrochloride, alprenolol hydrochloride, arotinolol hydrochloride, indenolol hydrochloride, oxprenolol hydrochloride, carteolol hydrochloride, pyrudicainide hydrochloride, bufetolol hydrochloride, bupranolol hydrochloride, procainamide hydrochloride, propafenone hydrochloride, propranolol hydrochloride, befunolol hydrochloride, verapamil hydrochloride, mexiletine hydrochloride, cibenzoline succinate, flecainide acetate, disopyramide, metoprolol tartrate, nadolol, pindolol, bisoprolol fumarate, timolol maleate, quinidine sulfate.

17. Diuretics:
Acetazolamide, azosemide, isosorbide, etacrynic acid, ethiazide, potassium canrenoate, quinethazone, clofenamide, chlorthalidone, cyclopenthiazide, spironolactone, theosalicin, triamterene, trichlormethiazide, hydrochlorothiazide, hydroflumethiazide, piretanide, bumetanide, furosemide, benzylhydrochlorothiazide, penflutizide, polythiazide, methyclothiazide, metolazone, mefruside.

18. Antihypertensive drugs:
Alacepril, alseroxylon, indapamide, urapidil, amosulalol hydrochloride, carteolol hydrochloride, guanfacine hydrochloride, clonidine hydrochloride, diltiazem hydrochloride, celiprolol hydrochloride, tilisolol hydrochloride, terazosin hydrochloride, delapril hydrochloride, todralazine hydrochloride, nicardipine hydrochloride, hydralazine hydrochloride, bunazosin hydrochloride, bunitrolol hydrochloride, prazosin hydrochloride, manidipine hydrochloride, labetalol hydrochloride, dimethylaminoethyl reserpilinate dihydrochloride, cadralazine, captopril, trimetaphan camsilate, guanabenz acetate, hexamethonium bromide, metoprolol tartrate, silazapuril, syrosingopine, tripamide, nadolol, nipradilol, nilvadipine, budralazine, enalapril maleate, dihydroergotoxine mesylate, doxazosin mesylate, phentolamine mesilate, meticrane, methyldopa, Rauwopur, ricinopuril, guanethidine sulfate, betanidine, sulfate, penbutolol sulfate, rescinnamine, reserpine, 2,6-dimethyl-4-(2-nitrophenyl)-5-(2-oxo-1,3,2-dioxaphosphorinan-2-yl)-1,4-dihydropyridine-3-carboxylate.

19. Vasoconstrictors:

Norfenefrine hydrochloride, phenylephrine hydrochloride, midodrine hydrochloride, methoxamine hydrochloride, dihydroergotamine mesylate.

20. Vasodilators:

Inositol hexanicotinate, efloxate, isoxsuprine hydrochloride, etafenone hydrochloride, oxyfedrine hydrochloride, carbocromen hydrochloride, dilazep dihydrochloride, trimetazidine hydrochloride, valnidipine hydrochloride, venidipine hydrochloride, verapamil hydrochloride, nicametate citrate, cyclandelate, pentaerythrityl tetranitrate, dipyridamole, isosorbide dinitrate, trapidil, nicorandil, nisoldipine, nitrendipine, nifedipine, hepronicate, bamethan sulfate, γ-oryzanol, clinofibrate, clofibrate, aluminium clofibrate, colestyramine, symvastatin, simfibrate, soysterol, dextran sulfate sodium, nicomol, niceritrol, pravastatin sodium, probucol, bezafibrate, polyenephos phatidylcholine, melinamide, ethyl linoleate.

21. Cardiovascular drugs:

Argatroban, alprostadil, ibudilast, flunarizine hydrochloride, meclofenoxate hydrochloride, moxisylyte hydrochloride, sodium ozagrel, citicoline, ifenprodil tartrate, cinnarizine, cytochrome C, tocopherol nicotinate, nicergoline, pyridinol carbamate, vinpocetine, nizofenone fumarate, brovincamine fumarate, bencyclane fumarate, pentoxifylline, calcium polystyrene sulfonate, sodium polystyrene sulfonate, cinepazide maleate, lisuride maleate, dihydroergotamine nesylate, amezinium methyl sulfate, limaprost α-cyclodextrin clathrate.

22. Respiratory stimulants:

Dimefline hydrochloride, doxapram hydrochrolide, naloxone hydrochloride, lobeline hydrochloride, dimorpholamine, levallorphan tartrate, flumazenil.

23. Antitussives:

Asdrin, clofedanol hydrochloride, clobutinol hydrochloride, fominoben hydrochloride, methylephedrine hydrochloride, isoaminile citrate, oxeladin citrate, pentoxyverine citrate, Chlophedrin S, chloperastine, dextromethorphan hydrochloride, oxeladin tannate, dl-methylephedrine hydrochloride, dl-methylephedrine, noscapine, dimemorfan phosphate, benproperine phosphate.

24. Expectorant's:

N-Acetyl-L-cysteine, ambro;ol hydrochloride, L-cysteine ethyl ester hydrochloride, bromhexine hydrochloride, carbocisteine, eprazinone hydrochloride, guaif enesin, tipepidine hibenzate, codeine phosphate, dihydrocodeine phosphate.

25. Brochodilators:

Epinephrine hydrochloride, clenbuterol hydrochloride, clorprenaline hydrochloride, tulobuterol hydrochloride, trimetoquinol hydrochloride, pirbuterol hydrochloride, procaterol hydrochloride, methoxyphenamine hydrochloride, sodium cromoglycate, diprophylline, fenoterol hydrobromide, theophylline, formoterol fumarate, isoproterenol sulfate, orciprenaline sulfate, salbutamol sulfate, terbutaline sulfate, hexoprenaline sulfate.

26. Antidiarrheal drugs/drugs for controlling intestinal function:

Berberine chloride, leperamide hydrochloride, dimethicone, bismuth subgallate, berberine tannate, lactomin, berberine sulfate.

27. Peptic ulcer remedies:

Aceglutamide aluminium, sodium alginate, aldioxa, L-glutamine, cetraxate hydrochloride, pirenzepine hydrochloride, ranitidine hydrochloride, rozatidine acetate hydrochloride, omeprazole, ornoprostil, chlophyllin S, gefarnate, Kolantyl, cimetidine, sucralfate, sulpiride, secretin, sofalcone, teprenone, troxipide, nizatidine, famotidine, plaunotol, proglumide, bergenin, irsogladine maleate, methylmethionine sulfonium chloride, clebopride malate, levamipil.

28. Stomachics/digestants:

Carnitine chloride.

29. Laxatives/clysters:

Bisoxatin acetate, sodium picosulfate, bisacodyl, lactulose.

30. Cholagogues:

Anetholtrithion, ursodesoxycholic acid, osalmid, chenodeoxycholic acid, dehydrocholic acid, trepibutone, hymecromone.

31. Gastrointestinal drugs:

Granisetron hydrochloride, cisapride, triamcinolone acetonide, tricaprilin, domperidone, fenipentol, trimebutine maleate, metoclopramide.

32. Thyroid/parathyroid hormone drugs:

Thiamazole, propylthiouracil, liothyronine sodium, levothyroxine sodium.

33. Anabolic steroid drugs:

Ethylnandrol, oxymetholone, nandrolone cyclohexane propionate, bolandiol dipropionate, stanozolol, nandrolone decanoate, nandrolone phenylpropionate, furazabol, nandrolone furylpropionate, mestanolone, meterolone.

34. Corticoid drugs:

Epinephrine, hydrocortisone sodium succinate, prednisolone sodium succinate, cortisone acetate, dexamethasone acetate, triamcinolone diacetate, parainethasone acetate, halopredone acetate, hydrocortisone acetate, fludrocortisone acetate, prednisolone acetate, methylprednisolone acetate, dexamethasone, triamcinolone, norepinephrine, dexamethasone palmitate, hydrocortisone, prednisolone butylacetate, prasterone sodium sulfate, prednisolone, beclometasone dipropionate, betamethasone, dexamethasone sodium metasulfobenzoate, methylprednisolone, dexamethasone sodium phosphate, hydrocortisone sodium phosphate, prednisolone sodium phosphate, betamethasone sodium phosphate.

35. Male hormone drugs:

Testosterone enanthate, fluoxymesterone, testosterone propionate, dromostanolone propionate, methyltestosterone.

36. Estrogen/progestin drugs:

Allylestrenol; estradiol benzoate, estriol benzoyldiacetate, estriol, ethinylestradiol, gestonorone caproate, hydroxyprogesteron caproate, estradiol valerate, chlormadinone acetate, medroxyprogestero ne acetate, dydrogesterone, estradiol dipropionate, dimethisterone, norethisterone, pregnanediol, progesterone, estriol tripropionate, fosfestrol, mestranol.

37. Hormone drugs other than 32–36:

Epitiostanol, oxendolone, clomifene citrate, glucagon, gemeprost, octreotide acetate, goserelin acetate, gonadorelin acetate, cyproterone acetate, buserelin acetate, leuprolerin acetate, cyclofenil, dinoprost, dinoprost tromethamine, dinoprostone, danazol, trilostane, mitotane, mepitiostane.

38. Urinary tract drugs:

Oxybutynin hydrochloride, flavoxate hydrochloride, Paraprost, hexamine.

39. Oxytocics:

Ergometrine maleate, methylergometrine maleate, sparteine sulfate.

40. Vitamins:

Alfacalcidol, etretinate, ergocalciferol, calcitriol, retinol acetate, dihydrotachysterol, retinol palmitate, cetotiamine hydrochloride, thiamine hydrochloride, cocarboxylase, thiamine nitrate, bisthiamine nitrate, thiamine disulfide, bisibuthiamine, bisbutytiamine, bisbentiamine, fursultiamine, prosultiamine, benfotiamine, pyridoxine hydrochloride, cobamamide, hydroxocobalamin acetate, cyanocobalamin, 'nicotinic acid, nicotinamide, pantethine, mecobalamin, folic acid, riboflavin butyrate, riboflavin, pyridoxamine phosphate, pyridoxal phosphate, riboflavin sodium phosphate, ascorbic acid, tocopherol calcium succinate, tocopherol acetate, phytonadione, menatetrenone, biotin.

41. Hemostatics:

Sodium alginate, ethamsylate, carbazochrome, carbazochrome sodium sulfonate, tranexamic acid, thrombin, adrenochrome monoaminoguanidine methanesulfonate.

42. Anticoagulants:

Dipyridamole, dalteparin sodium, heparin calcium, heparin sodium, warfarin potassium.

43. Liver disease remedies:

2-Aminoethanesulfonic acid, glucuronolactone, glucuronamide, sodium glucuronate, cianidanol, diisopropylamine dichloroacetate, thioctic acid, thioctic acid amide, tiopronin, protoporphyrin disodium, malotilate.

44. Antidotes: Calcium disodium edetate, glutathione, penicillamine, deferoxamine mesilate, pralidoxime iodide.

45. Arthrifuges:

Allopurinol, colchicine, sulfinpyrazone, probenecid, benzbromarone.

46. Antidiabetics:

Acetohexamide, buformine hydrochloride, metformin hydrochloride, gliclazide, glyclopyramide, glybuzole, glibenclamide, glymidine sodium, chlorpropamide, tolazamide, tolbutamide.

47. Metabolism drugs:

Azathioprine, adenosine triphosphate disodium, aprotinin, ipriflavone, urinastatin, disodium etidronate, epalrestat, elcatonin, L-cysteine, levocarnitine chloride, sapropterin hydrochloride, calcitonin, arginine glutamate, sodium glutamate, sodium chondroitin sulfate, ciclosporin, sodium hyaluronate, mizoribine, gabexate mesilate, camostat mesilate, nafamostat mesilate, lactulose.

48. Antitumor drugs:

Aceglatone, ifosfamide, ubenimex, enocitabine, procarbazine hydrochloride, mitoxantrone hydrochloride, nitrogen mustard N-oxide hydrochloride, nimustine hydrochloride, carboquone, carboplatin, carmofur, tamoxifen citrate, cyclophosphamide, cisplatin, cytarabine, sizofiran, dacarbazine, thiotepa, thioinosine, tegafur, improsulfan tosilate, doxifluridine, hydroxycarbamide, fluorouracil, busulfan, mitobronitol, melphalan, methotrexate, mercaptopurine, ranimustine, estramustine sodium phosphate, lentinan.

49. Antiallergic agents:

Amlexanox, azelartine hydrochloride, isothipendyl hydrochloride, iproheptine hydrochloride, ozagrel hydrochloride, diphenylpyraline hydrochloride, diphenhydramine hydrochloride, cyproheptadine hydrochloride, triprolidine hydrochloride, promethazine hydrochloride, homochlorcyclizine hydrochloride, oxatomide, glycyrrhizin, sodium cromoglycate, alimemazine tartrate, tazanolast, diphenhydramine tannate, diphenylpyraline teoclate, terfenadine, tranilast, pemirolast potassium, clemastine fumarate, chlorpheniramine maleate, dimethindene maleate, mequitazine.

50. Antibiotics:

Aspoxicillin, aztreonam, acetylkitasamycin, amoxicillin, ampicillin, erythromycin estolate, spectinomycin hydrochloride, oxytetracycline hydrochloride, cefotiam dihydrochloride, cefotiam hexetil hydrochloride, cefmenoxime hydrochloride, tetracycline hydrochloride, demethylchlortetracycline hydrochloride, doxycycline hydrochloride, vancomycin hydrochloride, pivmecillinam hydrochloride,. minocycline hydrochloride, lincomycin hydrochloride, carindacillin sodium, carumonam sodium, clarithromycin, griseofulvin, clindamycin, cloxacillin sodium, chloramphenicol, chloram phenicol sodium succinate, colistin sodium methanesulfonate, cycloserine, midecamycin acetate ciclacillin, cefazolin sodium, cefatrizine propylene glycol, cefapirin sodium, cefamandole sodium, cefalexin, cefafotin sodium, cefaloridine, cefixime, cefodizime sodium, cefotaxime sodium, cefdinir, cefuzonam sodium, ceftazidime, ceftizoxime sodium, ceftezole sodium, ceftriaxone sodium, cefsulodin sodium, cefminox sodium, cefradine, cefroxadine, cefuroxime axetil, cefuroxime sodium, tetracycline, sultamicillin tosilate, chloramphenicol palmitate, pheneticillin potassium, phenoxymethylpenicillin potassium, flucloxacillin sodium, josamycin propionate, flucloxacillin sodium, benzylpenicillin potassium, benzylpenicillin benzathine, fosfomycin, midecamycin, rifampicin, capreomycin sulfate, sisomicin sulfate, paromomycin sulfate, loxythromycin.

51. Sulfa drugs:

Acetylsulfamethoxazol, sulfadimethoxine, sulfamethizole, sulfamethoxazole, sulfamethopyrazine, sulfamonomethoxine, sulfisoxazole, sulfisomidine.

52. Antituberculosis drugs:

Isoniazid, isoniazid sodium glucuronate, isoniazid sodium methansulfonate, ethionamide, ethambutol hydrochloride, pyrazinamide.

53. Antileprotics: Sodium glucosulfone, diaphenylsulfone, thiazosulfone.

54. Synthetic antimicrobial agents:

Enoxacin, thiamphenicol glycinate hydrochloride, ciprofloxacin hydrochloride, lomefloxacin hydrochloride, ofloxacin, cinoxacin, thiamphenicol, tosfloxacin tosylate, nalidixic acid, norfloxacin, pipemidic acid trihydrate, 6-fluoro-1-methyl-7-[4-(5-methyl-2-oxo-1,3-dioxolen-4-yl) methyl-piperazinyl]-4-oxo-4H[1,3]-thiazeto[3,2-a] quinoline-3-carboxylic acid.

55. Antiviral agents:

Aciclovir, ganciclovir, zidanocin, vidarabine.

56. Chemotherapeutic drugs:

Inosine pranobex, nalidixic acid, fluconazole, flucytosine, miconazole.

57. Anthelmintics:

Kainic acid, diethylcarbamazine citrate, santonin, bithionol, praziquantel, piperazine phosphate.

58. Narcotics:

Ethylmorphine hydrochloride, cocaine hydrochloride, morphine hydrochloride, oximetebanol, fentanyl citrate, morphine sulfate, codeine phosphate, dihydrocodeine phosphate.

The usefulness of inducing a transition of the crystalline state of a crystallizable substance is pointed out below.

(1) By inducing a transition from metastable crystalline state or the like to stable crystalline state, the stability of a bulk substance or a pharmaceutical composition, for instance, can be increased.

(2) By inducing a transition from stable crystalline state or the like to metastable crystalline state or amorphous solid state, the solubility of a medicinal substance in the gastrointestinal tract can be increased and, hence, its bioavailability can be improved or modulated.

(3) By inducing a transition from crystalline state with a crystal habit to a different crystalline state, powder properties such as flowability and packing and compression characteristics in the granulation stage and tablet-machine compression stage can be improved.

Since the method of this invention is not a batch process but a continuous process, mass processing is feasible with small equipment.

Moreover, because it is a continuous process, the quantity of the medicinal substance actually processed within the equipment at any given time-point is small so that a biased transition of crystalline state due to a temperature gradient is little involved.

BEST MODE FOR CARRYING OUT THE INVENTION

The following examples and test example are intended to illustrate this invention in further detail.

It should be understood that the numbers assigned to the respective barrels are in the order starting with the barrel closest to the feeding side.

EXAMPLE 1

A twin-screw extruder (KEX-30S-20; manufactured by Kurimoto, Ltd.) equipped with a die having an orifice diameter of 5 mmφ was supplied with Form α-indomethacin (metastable crystals) at a feeding rate of 30 g/min., and using screws with a diameter of 32 mmφ, an effective L/D ratio of 20 and a screw pattern of 16P, 12P, 9.6P, 30 deg, 60 deg, 9.6P and 8P, and the temperature settings of barrel 1=25° C., barrel 2=155° C., barrel 3=155° C., barrel 4=155° C., barrel 5=50° C. and die=40° C., the load was extruded at a speed of 100 rpm to provide Form γ-indomethacin (stable crystals).

EXAMPLE 2

A twin-screw extruder (XEX-30S-20; manufactured by Kurimoto, Ltd.) equipped with a die having an orifice diameter of 5 mmφ was continuously charged with a mixture (1:1) of Form α-indomethacin (metastable crystals) and Form γ-indomethacin (stable crystals) at a feeding rate of 30 g/min. and using the same screws as described in Example 1 and the barrel and die temperature settings of barrel 1=25° C., barrel 2=155° C., barrel 3=155° C., barrel 4=155° C., barrel 5=50° C., and die=40° C., the load was processed and extruded at an extrusion speed of 100 rpm to provide homogeneous Form γ-indomethacin (stable crystals).

EXAMPLE 3

A twin-screw extruder (KEX-30S-20; manufactured by Kurimoto, Ltd.) equipped with a die having an orifice 2 mm high and 10 mm wide was fed with Form α-indomethacin (metastable crystals) at a feeding rate of 20 g/min. had using the same screws as described in Example 1 and the barrel and die temperature settings of barrel 1=25° C., barrel 2=155° C., barrel 3=155° C., barrel 4=155° C. and barrel 5=20° C., and die=10° C., the load was processed and extruded at an extrusion speed of 100 rpm to provide amorphous solid indomethacin.

EXAMPLE 4

A twin-screw extruder (KEX-30S-20; manufactured by Kurimoto, Ltd.) equipped with an orifice 2 mm high and 10 mm wide was continuously charged with Form γ-indomethacin (stable crystals) at a feeding rate of 20 g/min. and using the same screws as described in Example 1 and the barrel and die temperature settings of barrel 1=25° C., barrel 2=162° C., barrel 3=162° C., barrel 4=162° C., barrel 5=20° C., and die=10° C., the load was processed and extruded at an extrusion speed of 20 rpm to provide amorphous solid indomethacin.

EXAMPLE 5

A twin-screw extruder (KEX-30S-20; manufactured by Kurimoto, Ltd.) equipped with a die having an orifice diameter of 5 mmφ was supplied with Form I-bromovalerylurea (metastable crystals) at a feeding rate of 25 g/min. and using the same screws as described in Example 1 and the barrel and die temperature settings of barrel 1=25° C., barrel 2=147° C., barrel 3=147° C., barrel 4=147° C., barrel 5=90° C., and die=50° C., the load was processed and extruded at an extrusion speed of 100 rpm to provide Form II-bromovalerylurea (stable crystals).

EXAMPLE 6

An amorphous solid obtained by melting crystalline chloramphenicol palmitate and quenching the melt at −10° C. was fed to a twin-screw extruder (KEX-30s-20; manufactured by Kurimoto, Ltd.) equipped with a die having an orifice diameter of 5 mmφ at a feeding rate of 40 g/min. and using the same screws as described in Example 1 and the barrel and die temperature settings barrel of barrel 1=25° C., barrel 2=100° C., barrel 3=100° C., barrel 4=95° C., barrel 5=45° C. and die=45° C., the load was processed and extruded at an extrusion speed of 50 rpm to provide Form α-chloramphenicol palmitate (metastable crystals).

EXAMPLE 7

Form I-carbamazepine (metastable crystals) was fed to a twin-screw extruder (KEX-30S-20; manufactured by Kurimoto, Ltd.) equipped with a die having an orifice sized 2 mm high and 10 mm wide at a feeding rate of 25 g/min. and using the same screws as described in Example 1 and the barrel and die temperature settings of barrel 1=25° C., barrel 2=177° C., barrel 3=190° C., barrel 4=190° C., barrel 5=190° C. and die=100° C., the load was processed and extruded at an extrusion speed of 20 rpm to provide Form III-carbamazepine (stable crystals).

EXAMPLE 8

Form II-carbamazepine (metastable crystals) was fed to a twin-screw extruder (KEX-30S-20; manufactured by Kurimoto, Ltd.) equipped with a die having an orifice sized 2 mm high and 10 mm wide at a feeding rate of 30 g/min. and using the same screws as described in Example 1 and the barrel and die settings of barrel 1=25° C., barrel 2=150° C., barrel 3=150° C., barrel 4=150° C., barrel 5=150° C. and die=100° C., the load was processed and extruded at an extrusion speed of 30 rpm to provide Form III-carbamazepine (stable crystals).

Test Example 1

The crystals obtained in Example 1 were milled in a mortar and the powder X-ray diffraction pattern of a sample of the resultant finely divided powder (100 mesh pass) was determined. It was found that, as shown in FIG. 3, the starting Form α-indomethacin (metestable crystals) had been converted to Form γ-indomethacin (stable crystals).

Figure 3:
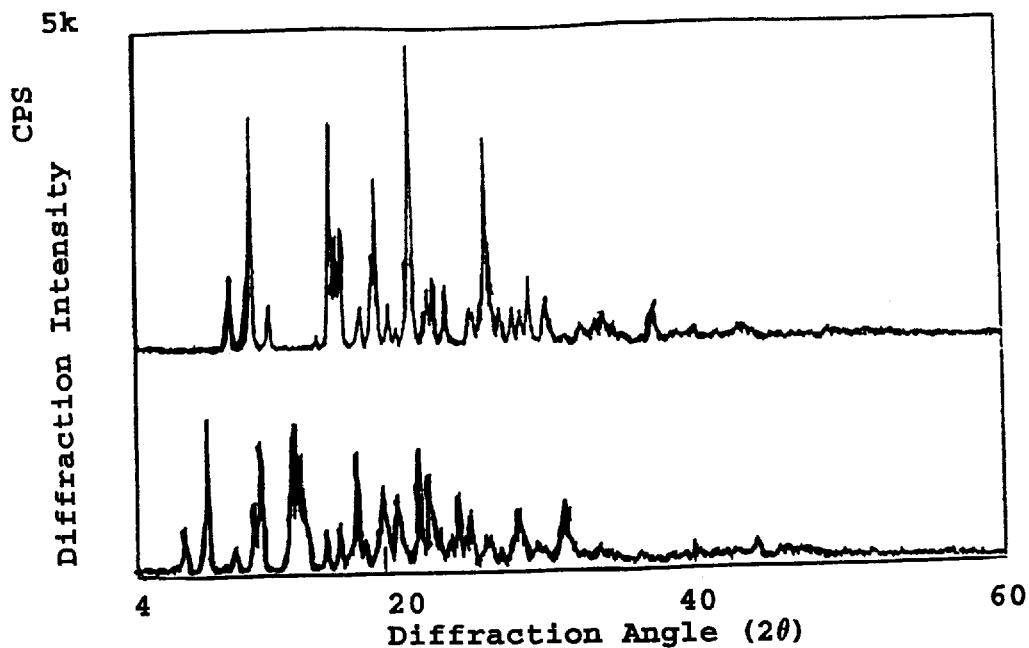
FIGS. 3–10 are powder diffraction patterns, with each figure showing comparative diffraction patterns for various substances prior to and after processing in accordance with the present invention.

The identification of the powder X-ray diffraction patterns of Form α- and γ-indomethacin samples shown in FIG. 3 was made according to the report of H. Yamamoto: Chem. Pham. Bull. (Tokyo), 16, 17 (1968).

Test Example 2

Figure 4:
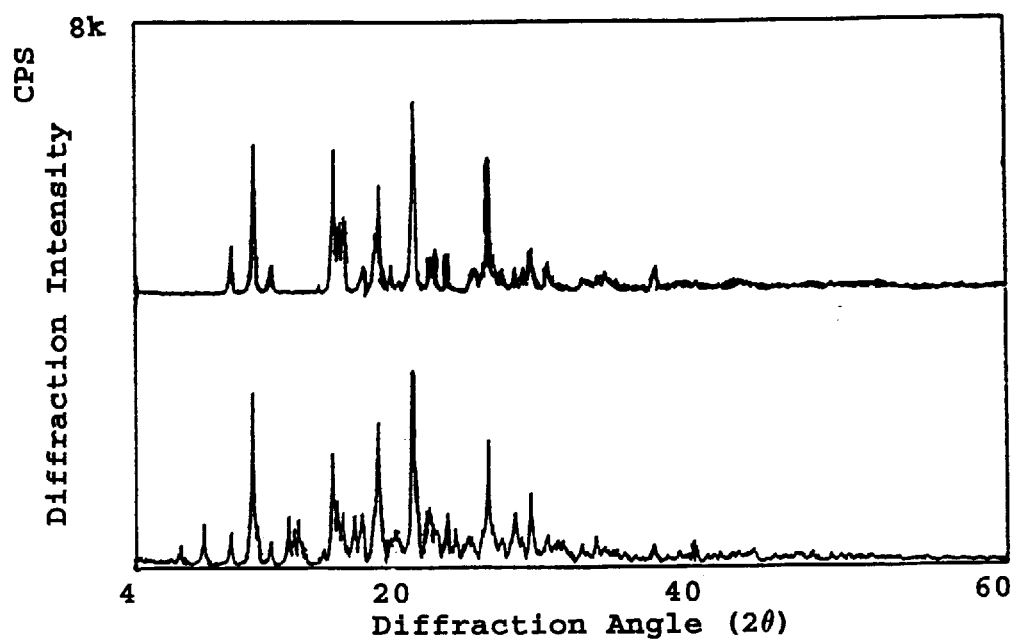

The crystals obtained in Example 2 were milled in a mortar and the powder X-ray diffraction pattern of a sample of the resultant finely divided powder (100 mesh pass) was determined. It could be confirmed that, as shown in FIG. 4, the diffraction peaks assignable to Form α-indomethacin had disappeared from the diffraction pattern of Form α-indomethacin (metastable crystals)-Form γ-indomethacin (stable crystals) mixture, suggesting the presence of Form γ-indomethacin alone. Identification of the powder X-ray diffraction patterns of Form α-indomethacin and Form γ-indomethacin shown in FIG. 4 was made according to the report of H. Yamamoto, Chem. Pham. Bull. (Tokyo), 16, 17 (1968).

Test Example 3

Figure 5:
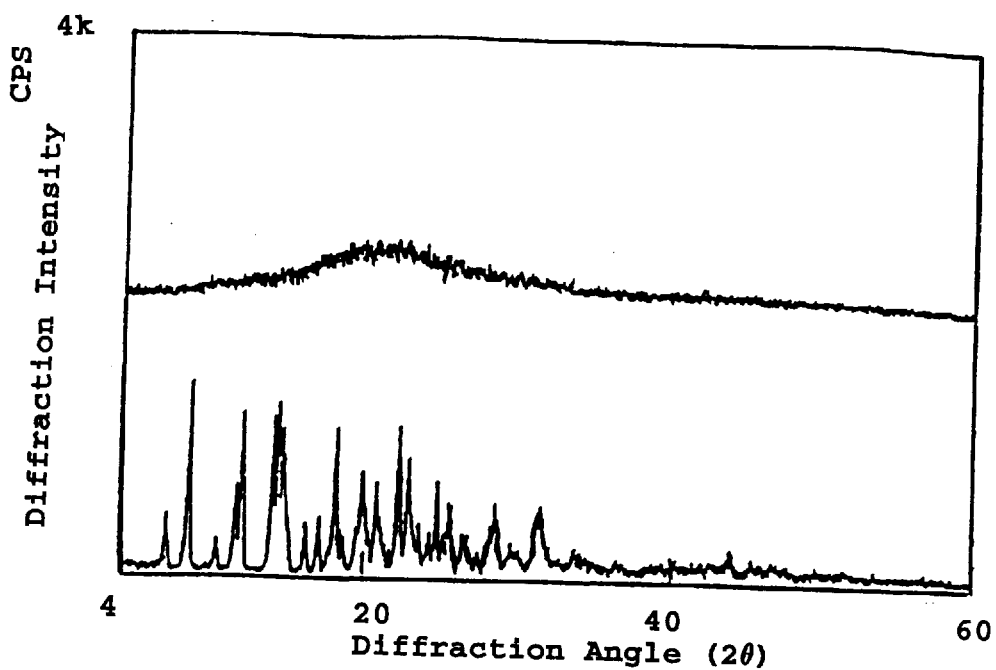

The solid obtained in Example 3 was milled in a mortar and the powder X-ray diffraction pattern of a sample of the resultant finely divided powder (100 mesh pass) was determined. As shown in FIG. 5, no diffraction peaks were observed, indicating that Form a indomethacin (metastable crystals) had been converted to an amorphous solid.

Test Example 4

Figure 6:
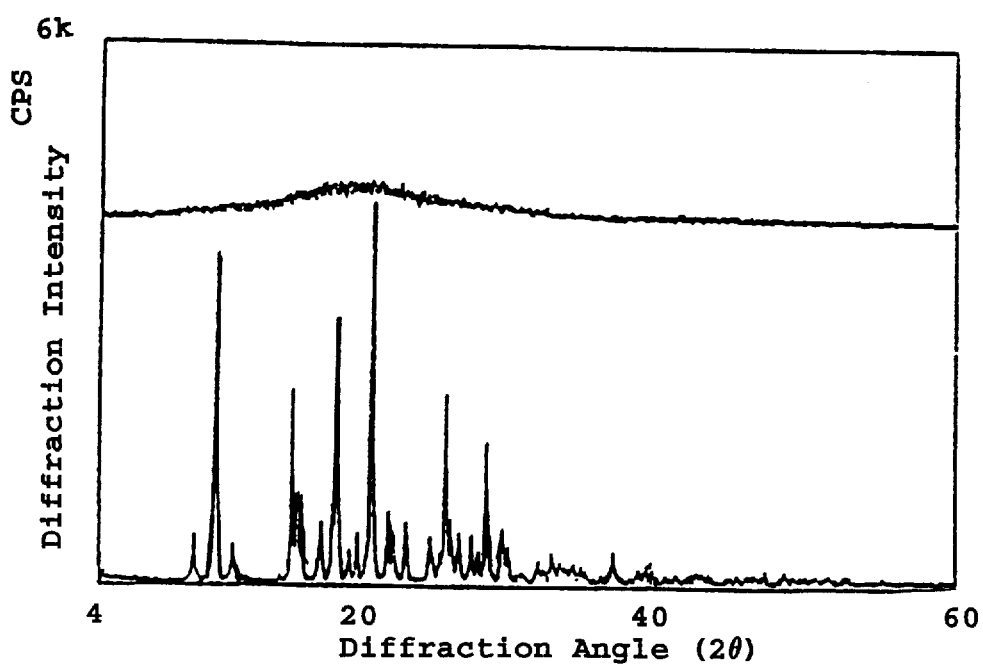

The solid obtained in Example 4 was milled in a mortar and the powder X-ray diffraction pattern of a sample of the resultant finely divided powder (100 mesh pass) was determined. As shown in FIG. 6, no diffraction peaks were observed, indicating that Form α-indomethacin (stable crystals) had been converted to an amorphous solid.

Test Example 5

Figure 7:
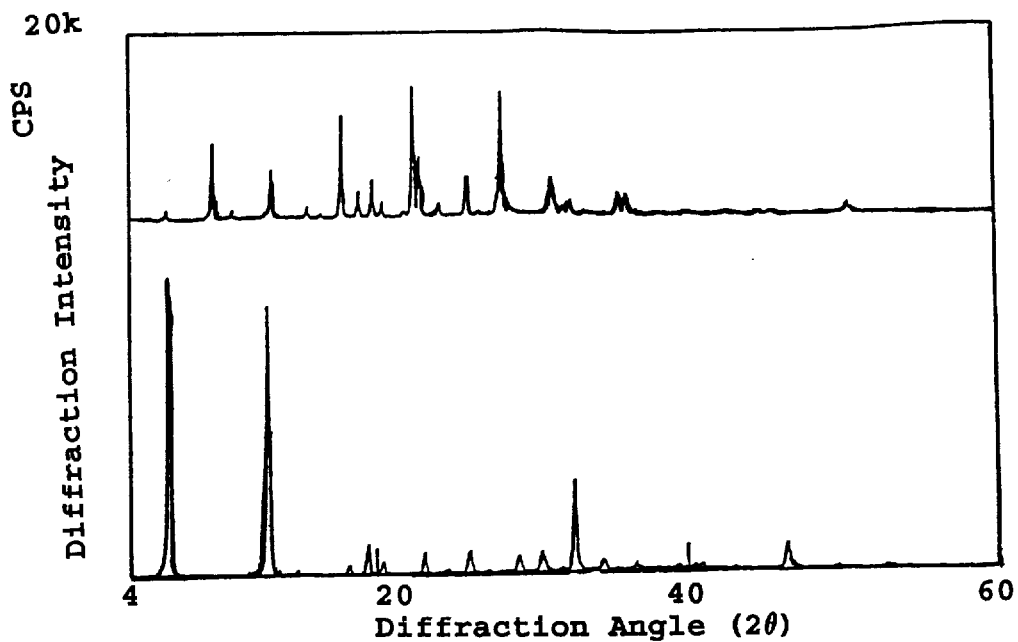

The crystals obtained in Example 5 were milled in a mortar and the powder X-ray diffraction pattern of a sample of the resultant finely divided powder (100 mesh pass) was determined. As shown in FIG. 7, Form I-bromovalerylurea (metestable crystal) had been converted to Form II-bromovalerylurea (stable crystals). Identification of the powder X-ray diffraction patterns of Form I-bromovalerylurea and Form II-bromovalerylurea shown in FIG. 7 was made according to the report of H. Kwada, Chem. Pharm. Bull., 28, 1351 (1980).

Test Example 6

The crystals obtained in Example 6 were milled in a mortar and the powder X-ray diffraction pattern of a sample of the resultant finely divided powder (100 mesh pass) was determined. It is clear from FIG. 8 that the amorphous solid chloramphenicol palmitate had been converted to Form α-chloramphenicol palmitate (metestable crystals). Identification of the powder X-ray diffraction patterns of amorphous solid chloramphenicol palmitate and Form α-chloramphenicol palmitate was made according to T. Tamura, Yakugaku Zasshi, 81, 759 (1961) and Y. Tsuda, Chem. Pharm. Bull., (Tokyo), 28, 947 (1980).

Test Example 7

The crystals obtained in Example 7 were milled in a mortar and the powder X-ray diffraction pattern of a sample of the resultant finely divided powder (100 mesh pass) was determined. It is apparent from FIG. 9 that Form I-carbamazepine (metestable crystals) had been converted to Form III-carbamazepine (stable crystals). Identification of the powder X-ray diffraction patterns of Form I-carbamazepine and Form III- carbamazepine shown in FIG. 9 was made according to T. Umeda, Yakugaku Zasshi, 104, 786 (1984).

Test Example 8

The crystals obtained in Example 8 were milled in a mortar and the powder X-ray diffraction pattern of a sample of the resultant finely divided powder (100 mesh pass) was determined. It is apparent from FIG. 10 that Form II-carbamazepine (metestable crystals) had been converted to Form III-carbamazepine (stable crystals). Identification of the powder X-ray diffraction patterns of Form II-carbamazepine and Form III-carbamazepine was made according to T. Umeda, Yakugaku Zasshi, 104, 786 (1984).

DETAILED DESCRIPTION OF THE DRAWINGS

FIG. 1 is a schematic cross-section view showing the main part of a universal extruder, wherein 1, 2 and 3 represent a barrel structure, a die, and a screw, respectively.

FIG. 2 is a schematic view showing one embodiment of the method of this invention, wherein Δ represents the crystalline state of a medicinal substance prior to transition, X represents a molten state of the same substance, and ○ represents the crystalline state of said substance after transition and the reference numeral 4 represents the processing part of the extruder.

FIG. 3 shows powder X-ray diffraction patterns. The abscissa represents the diffraction angle (2θ) and the ordinate represents the diffraction intensity (CPS). The top view is the powder X-ray diffraction pattern of the Form γ-indomethacin obtained in Example 1. The bottom view is the powder X-ray diffraction pattern of the Form α-indomethacin prior to the processing according to this invention.

FIG. 4 shows powder X-ray diffraction patterns. The abscissa represents the diffraction angle (2θ) and the ordinate represents the diffraction intensity (CPS). The top view is the powder X-ray diffraction pattern of the Form γ-indomethacin obtained in Example 2 and the bottom view is the powder X-ray diffraction pattern of the Form α- and γ-indomethacin mixture prior to the processing according to this invention.

FIG. 5 shows powder X-ray diffraction patterns. The abscissa represents the diffraction angle (2θ) and the ordinate represents the diffraction intensity (CPS). The top view is the powder X-ray diffraction pattern of the amorphous solid indomethacin obtained in Example 3. The bottom view is the powder X-ray diffraction pattern of the Form α-indomethacin prior to the processing according to this invention.

FIG. 6 shows powder X-ray diffraction patterns. The abscissa represents the diffraction angle (2θ) and the ordinate represents the diffraction intensity (CPS). The top view is the powder X-ray diffraction pattern of the amorphous solid indomethacin obtained in Example 4. The bottom view is the powder X-ray diffraction pattern of the Form γ-indomethacin prior to the processing according to this invention.

FIG. 7 shows powder X-ray diffraction patterns. The abscissa represents the diffraction angle (2θ) and the ordinate represents the diffraction intensity (CPS). The top view is the powder X-ray diffraction pattern of the Form II-bromovalerylurea obtained in Example 5. The bottom view is the powder X-ray diffraction pattern of the Form I-bromovalerylurea prior to the processing according to this invention.

Figure 8:
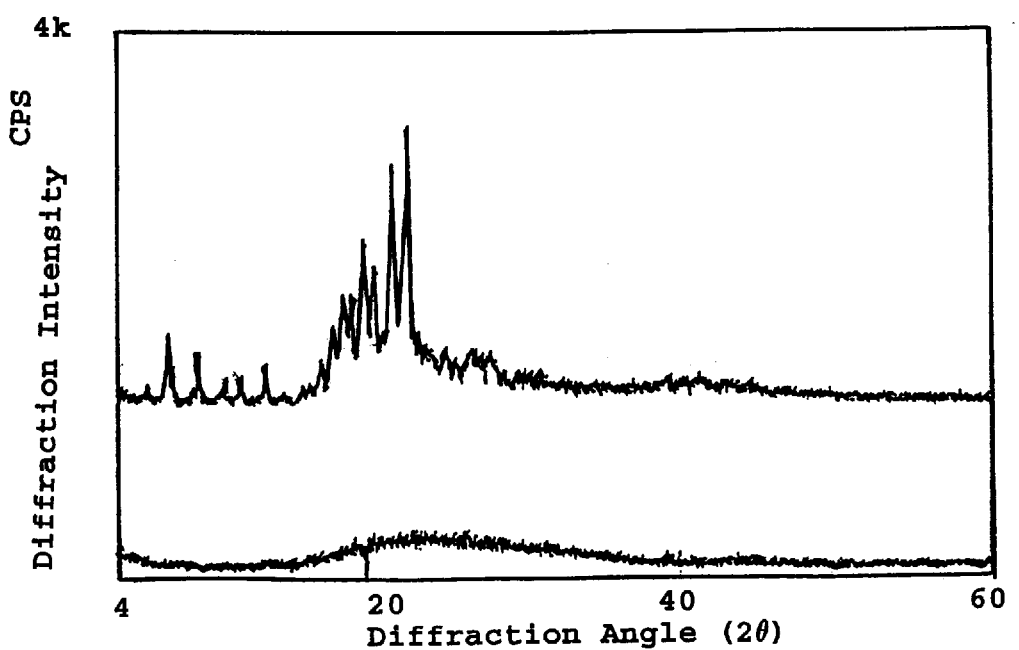

FIG. 8 shows powder X-ray diffraction patterns. The abscissa represents the diffraction angle (2θ) and the ordinate represents the diffraction intensity (CPS). The top view is the powder X-ray diffraction pattern of the Form α-chloramphenicol palmitate obtained in Example 6. The bottom view is the powder X-ray diffraction pattern of the chloramphenicol palmitate (amorphous solid) prior to the processing according to this invention.

Figure 9:
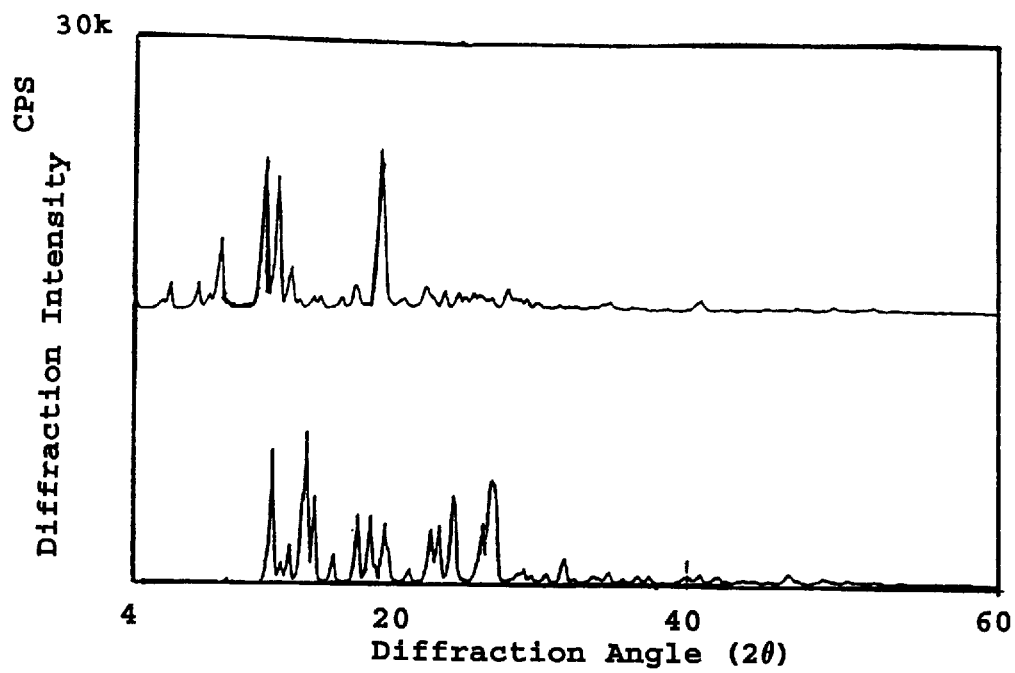

FIG. 9 shows powder X-ray diffraction patterns. The abscissa represents the diffraction angle (2θ) and the ordinate represents the diffraction intensity (CPS). The top view is the powder X-ray diffraction pattern of the Form III-carbamazepine obtained in Example 7.

The bottom view is the powder X-ray diffraction pattern of the Form I-carbamazepine prior to the processing according to this invention.

Figure 10:
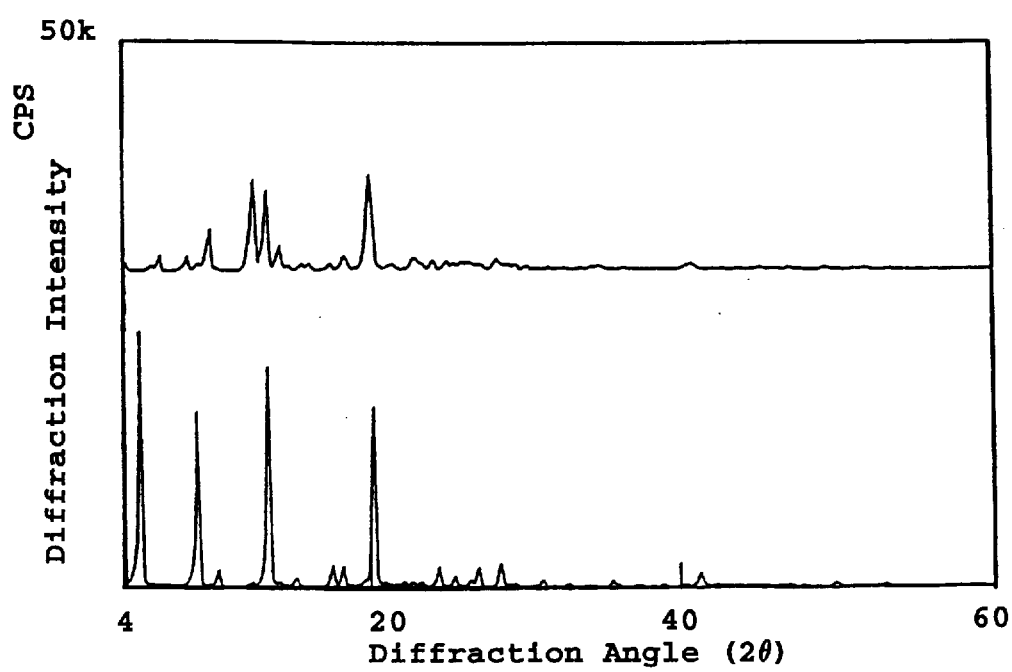

FIG. 10 shows powder X-ray diffraction patterns. The abscissa represents the diffraction angle (2θ) and the ordinate represents the diffraction intensity (CPS). The top view is the powder X-ray diffraction pattern of the Form III-carbamazepine obtained in Example 8. The bottom view is the powder X-ray diffraction pattern of the Form II-carbamazepine prior to the processing according to this invention.

We claim:

1. A method for inducing a transition from a first crystalline state to a second crystalline state in a crystallizable medicinal substance, said method comprising the steps of:
    a) feeding said substance, in the first crystalline state, into extruder means having at least two separate temperature zones, maintained at differing temperatures, with a first of said zones being maintained in a temperature range sufficient to melt the medicinal substance in the first crystalline state but below a decomposition temperature thereof, and with the second of said temperature zones being maintained in a temperature range below that of the first zone and at a level whereby the second crystalline state of the material is induced;
    b) melting the substance in the first crystalline state in said first zone and continuously moving the melted substance from the first zone to the second zone;
    c) inducing the second crystalline state in the crystallizable substance in said second zone; and
    d) extruding the substance, in said second crystalline state, from the extruder means.

2. The method of claim 1, wherein said extruder means comprises a single screw extruder, wherein a screw member effects the continuous moving of the medicinal substance from the first zone to the second zone, and wherein said extruder means further comprises a die, having at least one orifice through which the medicinal substance in the second crystalline state is extruded from the extruder means, and wherein the extruder means further comprises means for inducing the second crystalline state of the medicinal substance in said second zone to provide said inducing of the second crystalline state in the medicinal substance.

3. The method of claim 1, wherein said extruder means comprises a twin screw extruder, wherein intermeshed twin screw members effect the continuous moving of the medicinal substance from the first zone to the second zone, and wherein said extruder means further comprises a die, having at least one orifice through which the medicinal substance in the second crystalline state is extruded from the extruder means, and wherein the extruder means further comprises means for inducing the second crystalline state of the medicinal substance in said second zone to provide said inducing of the second crystalline state in the medicinal substance.

4. The method of claim 3, wherein said first crystalline state is a metastable crystalline state or an amorphous solid state and said second crystalline state is a stable crystalline state.

5. The method of claim 3, wherein said first crystalline state is a stable crystalline state or an amorphous solid state and said second crystalline state is a metastable crystalline state.

6. The method of claim 3, wherein said first crystalline state is a stable or metastable crystalline state and said second crystalline state is an amorphous solid state.

7. The method of claim 3, wherein said first crystalline state is a heterogeneous crystalline state and said second crystalline state is a homogeneous crystalline state.

8. The method of claim 3, wherein the medicinal substance is selected from the group consisting of general anesthetics; hipnotic/sedatives/antianxiety drugs; antiepileptics; antipyretic/analgesic/antiinflammatory agents; analeptic/antihypnotic agents; antiparkinsonian drugs; psychotropic/neurotropic drugs; CNS drugs; local anesthetics; skeletal muscle relaxants; autonomic drugs; antispasmodics; antivertigo drugs; sense organ drugs; cardiotonics; antiarrhythmic drugs; diuretics; antihypertensive drugs; vasoconstrictors; vasodilators; cardiovascular drugs; respiratory stimulants; antitussives; expectorants; brochodilators; antidiarrheal drugs/drugs for controlling intestinal function; peptic ulcer remedies; stomachics/digestants; laxatives/clysters; cholagogues; gastrointestinal drugs; thyroid/parathyroid hormone drugs; anabolic steroid drugs; corticoid drugs; male hormone drugs; estrogen/progestin drugs; hormone drugs other than thyroid/parathyroid hormone drugs, anabolic steroid drugs, corticoid drugs, male hormone drugs, and estrogen/progestin drugs; urinary tract drugs; oxytocics; vitamins; hemostatics; anticoagulants; liver disease remedies; antidotes; arthrifuges; antidiabetics; metabolism drugs; antitumor drugs; antiallergic agents; antibiotics; sulfa drugs; antituberculosis drugs; antileprotics; synthetic antimicrobial agents; antiviral agents; chemotherapeutic drugs; anthelmintics; and narcotics.

9. The method of claim 8, wherein said general anesthetics are selected from the group consisting of ketamine hydrochloride, thiamylal sodium, thiopental sodium, droperidol, said hipnotic/sedatives/antianxiety drugs are selected from the group consisting of amobarbital, alprazolam, estazolam, flurazepam hydrochloride, rilmazafone hydrochloride, oxazepam, oxazolam, cloxazolam, clotiazepam, clorazepate dipotassium, chlordiazepoxide, chlormezanone, diazepam, secobarbital sodium, zopiclone, triazolam, triclofos sodium, nitrazepam, nimetazepam, barbital, haloxazolam, phenobarbital, prazepam, fludiazepam, flutazolam, flutoprazepam, flunitrazepam, flurazepam, brotizolam, bromazepam, bromovalerylurea, hexobarbital, perlapine, pnetobarbiturate, midazolam, mexazolan:, medazepam, ethyl loflazepate, lorazepam, lormetazepam, said antiepileptics are selected from the group consisting of acetylpheneturide, ethosuximide, ethotoin, carbamazepine, clonazepam, sultiame, zonisamide, trimethadione, sodium valproate, phenytoin sodium, primidone, metharbital, said antipyretic/analgesic/ antiinflammatory agents are selected from the group consisting of aspirin, aspirin DL-lysine, aspirin aluminum, acetaminophen, acemetacin, alclofenac, alminoprofen, amfenac sodium, isopropylantipyrine, ibuprofen, indomethacin, indomethacin farnesil, ethenzamide, epirizole, emorfazone, tiaramide hydrochloride, tinoridine hydrochloride, tramadol hydrochloride, buprenorphine hydrochloride, benzydamine hydrochloride, oxaprozin, clofezone, ketophenylbutazone, ketoprofen, sasapyrine, salicylamide, choline salicylate, sodium salicylate, Saridon, diclofenac sodium, diflunisal, eptazocine hydrobromide, butorphanol tartrate, sulindac, sulpyrine, tiaprofenic acid, tenoxicam, tolfenamic acid, tolmetin sodium, nabumetone, naproxen, Neo vitacain, Neurotropin, bitoxin, piroxicam, phenacetin, phenylacetylglycine, phenylbutazone, fenoprofen calcium, fenbufen, bucolome, pranoprofen, flufenamic acid, flufenamic acid aluminium, flurbiprofen, flurbiprofenaxetil, floctafenine, pentazocine, proglumetacin maleate, migrenin, dimetotiazine mesilate, metiazinic acid, mefenamic acid, loxoprofen sodium, lobenzarit disodium, said analeptic/antihypnotic agents are selected from the group consisting of methamphetamine hydrochloride, bemegride, said antiparkinsonian drugs are selected from the group consisting of amantadine hydrochloride, trihexyphenidyl hydrochloride, piroheptine hydrochloride, mazaticol hydrochloride, methixene hydrochloride, droxidopa, biperiden, bromocriptine mesilate, levodopa, said psychotropic/neurotropic drugs are selected from the group consisting of amoxapine, etizolam, amitriptyline hydrochloride, imipramine hydrochloride, clocapramine dihydrochloride, clomipramine hydrochloride, safrazine hydrochloride, sultopride hydrochloride, thioridazine hydrochloride, desipramine hydrochloride, dosulepin hydrochloride, trazodone hydrochloride, triflupromazine hydrochloride, nortriptyline hydrochloride, hydroxyzine hydrochloride, pipamperone hydrochloride, pipradorol hydrochloride, maprotiline hydrochloride, mianserin hydrochloride, methylphenidate hydrochloride, mosapramine hydrochloride, moperone hydrochloride, lofepramine hydrochloride, oxypertine, carpipramine, clotiapine, chlorprothixene, chlorpromazine, thioproperazine dimethansulfonate, spiperone, sulpiride, zotepine, tiotixene, timiperone, haloperidol decanoate, nemonapride, hydroxyzine pamoate, haloperidol, pimozide, fluphenazine, prochlorperazine, propericyazine, bromazepam, bromperidol, pemoline, perphenazine, cetipriline maleate, trifluoperazine maleate, trimipramine maleate, reserpine, levomepromazine, said CNS drugs are selected from the group consisting of idebenone, amantadine hydrochloride, indeloxazine hydrochloride, cyproheptadine hydrochloride, tiapride hydrochloride, bifemelane hydrochloride, meclofenoxate hydrochloride, lefetamine hydrochloride, τ-amino-β-hydroxybutyric acid, citicoline, protirelin tartrate, baclofen, propentofylline, calcium hopantenate, mazindol, said local anesthetics are selected from the group consisting of ethyl aminobenzoate, oxybuprocaine hydrochloride, dibucaine hydrochloride, tetracaine hydrochloride, p-butylaminobenzoyldiethyl aminoethanol hydrochloride, bupivacaine hydrochloride, procaine hydrochloride, propitocaine hydrochloride, mepivacaine hydrochloride, oxethazaine, ethyl p-piperidinoacetyl aminobenzoate, lidocaine hydrochloride, said skeletal muscle relaxants are selected from the group consisting of alcuronium chloride, suxamethonium chloride, tubocurarine chloride, chlorphenesin carbamate, chlorzoxazone, chlormezanone, pancuronium bromide, vecuronium bromide, dantrolene sodium, phenprobamate, pridinol mesylate, methocarbamol, said autonomic drugs are selected from the group consisting of acetylcholine chloride, ambenonium chloride, carpronium chloride, trospium chloride, bethanechol chloride, oxyphencyclimine hydrochloride, dicycloverin hydrochloride, tolazoline hydrochloride, distigmine bromide, valethamate bromide, pyridostigmine bromide, prifinium bromide, propantheline bromide, mepenzolate bromide, tofisopam, aclatonium napadisilate, neostigmine, oxapium iodide, diphenylpiperidinomethyldioxolane iodide, said antispasmodics are selected from the group consisting of afloqualone, etomidoline, isoxsuprine hydrochloride, eperisone hydrochloride, tizanidine hydrochloride, tolperisone hydrochloride, papaverine hydrochloride, piperidolate hydrochloride, bromoethyl pipethanate, scopolamine hydrobromide, timepidium bromide, valethamate bromide, butylscopolamine bromide, atropine methobromide, anisotropine methobromide, benactyzium methobromide, baclofen, flopropione, metyrapone, N-methyl-scopolamine methyl sulfate, atropine sulfate, said antivertigo drugs are selected from the group consisting of isoprenaline hydrochloride, difenidol hydrochloride, meclizine hydrochloride, dimenhydrinate, thiethylperazine, promethazine theoclate and, betahistine mesylate, said sense organ drugs are selected from the group consisting of oxymetazoline hydrochloride, tetrizoline, said cardiotonics are selected from the group consisting of 2-aminoethanesulfonic acid, aminophylline, caffeine-sodium benzoate, etilefrine hydrochloride, ephedrine hydrochloride, dopamine hydrochloride, dobutamine hydrochloride, bucumolol hydrochloride, choline theophylline, diisobutylaminobenzoyloxypropyl theophylline, digitoxin, digoxin, diprophylline, metaraminol bitartrate, deslanoside, denopamine, trans-π-oxocamphor, bucladesine sodium, proxyphylline, proscillaridin, besnalinone, metildigoxin, ubidecarenone, lanatoside C, said antiarrhythmic drugs are selected from the group consisting of ajmaline, atenolol, acebutolol hydrochloride, aprindine hydrochloride, alprenolol hydrochloride, arotinolol hydrochloride, indenolol hydrochloride, oxprenolol hydrochloride, carteolol hydrochloride, pyrudicainide hydrochloride, bufetolol hydrochloride, bupranolol hydrochloride, procainamide hydrochloride, propafenone hydrochloride, propranolol hydrochloride, befunolol hydrochloride, verapamil hydrochloride, mexiletine hydrochloride, cibenzoline succinate, flecainide acetate, disopyramide, metoprolol tartrate, nadolol, pindolol, bisoprolol fumarate, timolol maleate, quinidine sulfate, said diuretics are selected from the group consisting of acetazolamide, azosemide, isosorbide, etacrynic acid, ethiazide, potassium canrenoate, quinethazone, clofenamide, chlorthalidone, cyclopenthiazide, spironolactone, theosalicin, triamterene, trichlormethiazide, hydrochlorothiazide, hydroflumethiazide, piretanide, bumetanide, furosemide, benzylhydrochlorothiazide, penflutizide, polythiazide, methyclothiazide, metolazone, mefruside, said antihypertensive drugs are selected from the group consisting of alacepril, alseroxylon, indapamide, urapidil, amosulalol hydrochloride, carteolol hydrochloride, guanfacine hydrochloride, clonidine hydrochloride, diltiazem hydrochloride, celiprolol hydrochloride, tilisolol hydrochloride, terazosin hydrochloride, delapril hydrochloride, todralazine hydrochloride, nicardipine hydrochloride, hydralazine hydrochloride, bunazosin hydrochloride, bunitrolol hydrochloride, prazosin hydrochloride, manidipine hydrochloride, labetalol hydrochloride, dimethylaminoethyl reserpilinate dihydrochloride, cadralazine, captopril, trimetaphan camsilate, guanabenz acetate, hexamethonium bromide, metoprolol tartrate, silazapuril, syrosingopine, tripamide, nadolol, nipradilol, nilvadipine, budralazine, enalapril maleate, dihydroergotoxine mesylate, doxazosin mesylate, phentolamine mesilate, meticrane, methyldopa, Rauwopur, ricinopuril, guanethidine sulfate, betanidine, sulfate, penbutolol sulfate, rescinnamine, reserpine, 2,6-dimethyl-4-(2-nitrophenyl)-5-(2-oxo-1,3,2-dioxaphosphorinan-2-yl)-1,4-dihydropyridine-3-carboxylate, said vasoconstrictors are selected from the group consisting of norfenefrine hydrochloride, phenylephrine hydrochloride, midodrine hydrochloride, methoxamine hydrochloride, dihydroergotamine mesylate, said vasodilators are selected from the group consisting of inositol hexanicotinate, efloxate, isoxsuprine hydrochloride, etafenone hydrochloride, oxyfedrine hydrochloride, carbocromen hydrochloride, dilazep dihydrochloride, trimetazidine hydrochloride, valnidipine hydrochloride, venidipine hydrochloride, verapamil hydrochloride, nicametate citrate, cyclandelate, pentaerythrityl tetranitrate, dipyridamole, isosorbide dinitrate, trapidil, nicorandil, nisoldipine, nitrendipine, nifedipine, hepronicate, bamethan sulfate, τ-oryzanol, clinofibrate, clofibrate, aluminium clofibrate, colestyramine, symvastatin, simfibrate, soysterol, dextran sulfate sodium, nicomol, niceritrol, pravastatin sodium, probucol, bezafibrate, polyenephos phatidylcholine, melinamide, ethyl linoleate, said cardiovascular drugs are selected from the group consisting of argatroban, alprostadil, ibudilast, flunarizine hydrochloride, meclofenoxate hydrochloride, moxisylyte hydrochloride, sodium ozagrel, citicoline, ifenprodil tartrate, cinnarizine, cytochrome C, tocopherol nicotinate, nicergoline, pyridinol carbamate, vinpocetine, nizofenone fumarate, brovincamine fumarate, bencyclane fumarate, pentoxifylline, calcium polystyrene sulfonate, sodium polystyrene sulfonate, cinepazide maleate, lisuride maleate, dihydroergotamine nesylate, amezinium methyl sulfate, limaprost α-cyclodextrin clathrate, said respiratory stimulants are selected from the group consisting of dimefline hydrochloride, doxapram hydrochrolide, naloxone hydrochloride, lobeline hydrochloride, dimorpholamine, levallorphan tartrate, flumazenil, said antitussives are selected from the group consisting of asdrin, clofedanol hydrochloride, clobutinol hydrochloride, fominoben hydrochloride, methylephedrine hydrochloride, isoaminile citrate, oxeladin citrate, pentoxyverine citrate, Chlophedrin S, chloperastine, dextromethorphan hydrochloride, oxeladin tannate, dl-methylephedrine hydrochloride, dl-methylephedrine, noscapine, dimemorfan phosphate, benproperine phosphate, said expectorants are selected from the group consisting of N-Acetyl-L-cysteine, ambroxol hydrochloride, L-cysteine ethyl ester hydrochloride, bromhexine hydrochloride, carbocisteine, eprazinone hydrochloride, guaifenesin, tipepidine hibenzate, codeine phosphate, dihydrocodeine phosphate, said brochodilators are selected from the group consisting of epinephrine hydrochloride, clenbuterol hydrochloride, clorprenaline hydrochloride, tulobuterol hydrochloride, trimetoguinol hydrochloride, pirbuterol hydrochloride, procaterol hydrochloride, methoxyphenamine hydrochloride, sodium cromoglycate, diprophylline, fenoterol hydrobromide, theophylline, formoterol fumarate, isoproterenol sulfate, orciprenaline sulfate, salbutamol sulfate, terbutaline sulfate, hexoprenaline sulfate, said antidiarrheal drugs/drugs for controlling intestinal function are selected from the group consisting of berberine chloride, leperamide hydrochloride, dimethicone, bismuth subgallate, berberine tannate, lactomin, berberine sulfate, said peptic ulcer remedies are consisting of the group consisting of aceglutamide aluminium, sodium alginate, aldioxa, L-glutamine, cetraxate hydrochloride, pirenzepine hydrochloride, ranitidine hydrochloride, roxatidine acetate hydrochloride, omeprazole, ornoprostil, chlophyllin S, gefarnate, Kolantyl, cimetidine, sucralfate, sulpiride, secretin, sofalcone, teprenone, troxipide, nizatidine, famotidine, plaunotol, proglumide, bergenin, irsogladine maleate, methylmethionine sulfonium chloride, clebopride malate, levamipil, said stomachics/digestants are consisting of the group consisting of carnitine chloride, said laxatives/clysters are consisting of the group consisting of bisoxatin acetate, sodium picosulfate, bisacodyl, lactulose, said cholagogues are consisting of the group consisting of anetholtrithion, ursodesoxycholic acid, osalmid, chenodeoxycholic acid, dehydrocholic acid, trepibutone, hymecromone, said gastrointestinal drugs are consisting of the group consisting of granisetron hydrochloride, cisapride, triamcinolone acetonide, tricaprilin, domperidone, fenipentol, trimebutine maleate, metoclopramide, said thyroid/parathyroid hormone drugs are consisting of the group consisting of thiamazole, propylthiouracil, liothyronine sodium, levothyroxine sodium, said anabolic steroid drugs are consisting of the group consisting of ethylnandrol, oxymetholone, nandrolone cyclohexane propionate, bolandiol dipropionate, stanozolol, nandrolone decanoate, nandrolone phenylpropionate, furazabol, nandrolone furylpropionate, mestanolone, metenolone, said corticoid drugs are consisting of the group consisting of epinephrine, hydrocortisone sodium succinate, prednisolone sodium succinate, cortisone acetate, dexamethasone acetate, triamcinolone diacetate, paramethasone acetate, halopredone acetate, hydrocortisone acetate, fludrocortisone acetate, prednisolone acetate, methylprednisolone acetate, dexamethasone, triamcinolone, norepinephrine, dexamethasone palmitate, hydrocortisone, prednisolone butylacetate, prasterone sodium sulfate, prednisolone, beclometasone dipropionate, betamethasone, dexamethasone sodium metasulfobenzoate, methylprednisolone, dexamethasone sodium phosphate, hydrocortisone sodium phosphate, prednisolone sodium phosphate, betamethasone sodium phosphate, said male hormone drugs are consisting of the group consisting of testosterone enanthate, fluoxymesterone, testosterone propionate, dromostanolone propionate, methyltestosterone, said estrogen/progestin drugs are consisting of the group consisting of allylestrenol, estradiol benzoate, estriol benzoyldiacetate, estriol, ethinylestradiol, gestonorone caproate, hydroxyprogesteron caproate, estradiol valerate, chlormadinone acetate, medroxyprogestero ne acetate, dydrogesterone, estradiol dipropionate, dimethisterone, norethisterone, pregnanediol, progesterone, estriol tripropionate, fosfestrol, mestranol, said hormone drugs other than thyroid/parathyroid hormone drugs, anabolic steroid drugs, corticoid drugs, male hormone drugs, and estrogen/progestin drugs are consisting of the group consisting of epitiostanol, oxendolone, clomifene citrate, glucagon, gemeprost, octreotide acetate, goserelin acetate, gonadorelin acetate, cyproterone acetate, buserelin acetate, leuprolerin acetate, cyclofenil, dinoprost, dinoprost tromethamine, dinoprostone, danazol, trilostane, mitotane, mepitiostane, said urinary tract drugs are consisting of the group consisting of oxybutynin hydrochloride, flavoxate hydrochloride, Paraprost, hexamine, said oxytocics are consisting of the group consisting of ergometrine maleate, methylergometrine maleate, sparteine sulfate, said vitamins are consisting of the group consisting of alfacalcidol, etretinate, ergocalciferol, calcitriol, retinol acetate, dihydrotachysterol, retinol palmitate, cetotiamine hydrochloride, thiamine hydrochloride, cocarboxylase, thiamine nitrate, bisthiamine nitrate, thiamine disulfide, bisibuthiamine, bisbutytiamine, bisbentiamine, fursultiamine, prosultiamine, benfotiamine, pyridoxine hydrochloride, cobamamide, hydroxocobalamin acetate, cyanocobalamin, nicotinic acid, nicotinamide, pantethine, mecobalamin, folic acid, riboflavin butyrate, riboflavin, pyridoxamine phosphate, pyridoxal phosphate, riboflavin sodium phosphate, ascorbic acid, tocopherol calcium succinate, tocopherol acetate, phytonadione, menatetrenone, biotin, said hemostatics are consisting of the group consisting of sodium alginate, ethamsylate, carbazochrome, carbazochrome sodium sulfonate, tranexamic acid, thrombin, adrenochrome monoaminoguanidine methanesulfonate, said anticoagulants are consisting of the group consisting of dipyridamole, dalteparin sodium, heparin calcium, heparin sodium, warfarin potassium, said liver disease remedies is consisting of the group consisting of 2-Aminoethanesulfonic acid, glucuronolactone, glucuronamide, sodium glucuronate, cianidanol, diisopropylamine dichloroacetate, thioctic acid, thioctic acid amide, tiopronin, protoporphyrin disodium, malotilate, said antidotes are consisting of the group consisting of calcium disodium edetate, glutathione, penicillamine, deferoxamine mesilate, pralidoxime iodide, said arthrifuges are consisting of the group consisting of allopurinol, colchicine, sulfinpyrazone, probenecid, benzbromarone, said antidiabetics are consisting of the group consisting of acetohexamide, buformine hydrochloride, metformin hydrochloride, gliclazide, glyclopyramide, glybuzole, glibenclamide, glymidine sodium, chlorpropamide, tolazamide, tolbutamide, said metabolism drugs are consisting of the group consisting of azathioprine, adenosine triphosphate disodium, aprotinin, ipriflavone, urinastatin, disodium etidronate, epalrestat, elcatonin, L-cysteine, levocarnitine chloride, sapropterin hydrochloride, calcitonin, arginine glutamate, sodium glutamate, sodium chondroitin sulfate, ciclosporin, sodium hyaluronate, mizoribine, gabexate mesilate, camostat mesilate, nafamostat mesilate, lactulose, said antitumor drugs are consisting of the group consisting of aceglatone, ifosfamide, ubenimex, enocitabine, procarbazine hydrochloride, mitoxantrone hydrochloride, nitrogen mustard N-oxide hydrochloride, nimustine hydrochloride, carboquone, carboplatin, carmofur, tamoxifen citrate, cyclophosphamide, cisplatin, cytarabine, sizofiran, dacarbazine, thiotepa, thioinosine, tegafur, improsulfan tosilate, doxifluridine, hydroxycarbamide, fluorouracil, busulfan, mitobronitol, melphalan, methotrexate, mercaptopurine, ranimustine, estramustine sodium phosphate, lentinan, said antiallergic agents are consisting of the group consisting of amlexanox, azelastine hydrochloride, isothipendyl hydrochloride, iroheptine hydrochloride, ozagrel hydrochloride, diphenylpyraline hydrochloride, diphenhydramine hydrochloride, cyproheptadine hydrochloride, triprolidine hydrochloride, promethazine hydrochloride, homochlorcyclizine hydrochloride, oxatomide, glycyrrhizin, sodium cromoglycate, alimemazine tartrate, tazanolast, diphenhydramine tannate, diphenylpyraline teoclate, terfenadine, tranilast, pemirolast potassium, clemastine fumarate, chlorpheniramine maleate, dimethindene maleate, mequitazine, said antibiotics are consisting of the group consisting of aspoxicillin, aztreonam, acetylkitasamycin, amoxicillin, ampicillin, erythromycin estolate, spectinomycin hydrochloride, oxytetracycline hydrochloride, cefotiam dihydrochloride, cefotiam hexetil hydrochloride, cefmenoxime hydrochloride, tetracycline hydrochloride, demethylchlortetracycline hydrochloride, doxycycline hydrochloride, vancomycin hydrochloride, pivmecillinam hydrochloride, minocycline hydrochloride, lincomycin hydrochloride, carindacillin sodium, carumonam sodium, clarithromycin, griseofulvin, clindamycin, cloxacillin sodium, chloramphenicol, chloram phenicol sodium succinate, colistin sodium methanesulfonate, cycloserine, midecamycin acetate ciclacillin, cefazolin sodium, cefatrizine propylene glycol, cefapirin sodium, cefamandole sodium, cefalexin, cefalotin sodium, cefaloridine, cefixime, cefodizime sodium, cefotaxime sodium, cefdinir, cefuzonam sodium, ceftazidime, ceftizoxime sodium, ceftezole sodium, ceftriaxone sodium, cefsulodin sodium, cefminox sodium, cefradine, cefroxadine, cefuroxime axetil, cefuroxime sodium, tetracycline, sultamicillin tosilate, chloramphenicol palmitate, pheneticillin potassium, phenoxymethylpenicillin potassium, flucloxacillin sodium, josamycin propionate, flucloxacillin sodium, benzylpenicillin potassium, benzylpenicillin benzathine, fosfomycin, midecamycin, rifampicin, capreomycin sulfate, sisomicin sulfate, paromomycin sulfate, loxythromycin, said sulfa drugs are consisting of the group consisting of acetylsulfamethoxazol, sulfadimethoxine, sulfamethizole, sulfamethoxazole, sulfamethopyrazine, sulfamonomethoxine, sulfisoxazole, sulfisomidine, said antituberculosis drugs are consisting of the group consisting of Isoniazid, isoniazid sodium glucuronate, isoniazid sodium methansulfonate, ethionamide, ethambutol hydrochloride, pyrazinamide, said antileprotics are consisting of the group consisting of sodium glucosulfone, diaphenylsulfone, thiazosulfone, said synthetic antimicrobial agents are consisting of the group consisting of enoxacin, thiamphenicol glycinate hydrochloride, ciprofloxacin hydrochloride, lomefloxacin hydrochloride, ofloxacin, cinoxacin, thiamphenicol, tosfloxacin tosylate, nalidixic acid, norfloxacin, pipemidic acid trihydrate, 6-fluoro-1-methyl- 7-[4-(5-methyl-2-oxo-1,3-dioxolen-4-yl) methylpiperazinyl]-4-oxo-4H[1,3]-thiazeto[3,2-a] quinoline-3-carboxylic acid, said antiviral agents are consisting of the group consisting of aciclovir, ganciclovir, zidanocin, vidarabine, said chemotherapeutic drugs are consisting of the group consisting of inosine pranobex, nalidixic acid, fluconazole, flucytosine, miconazole, said anthelmintics are consisting of the group consisting of kainic acid, diethylcarbamazine citrate, santonin, bithionol, praziquantel, piperazine phosphate, and said narcotics are selected from the group consisting of ethylmorphine hydrochloride, cocaine hydrochloride, morphine hydrochloride, oximetebanol, fentanyl citrate, morphine sulfate, codeine phosphate, dihydrocodeine phosphate.

10. The method of claim 9, wherein said medicinal substance is selected from the group consisting of indomethacin, bromovalerylurea, chloramphenicol palmitate, and carbamazepine.

11. The method of claim 3, wherein the means for inducing the second crystalline state comprises the intermeshing of the twin screw members whereby there is a high energy physical output in shearing and blending the medicinal substance.

12. The method of claim 11, wherein said means for inducing the second crystalline state members further includes at least one kneading paddle, extending between said twin screws such that the medicinal substance is compounded thereby to facilitate effecting the inducing of the second crystalline state.

* * * * *